(12) United States Patent
Abidin

(10) Patent No.: US 8,221,798 B1
(45) Date of Patent: Jul. 17, 2012

(54) PHARMACEUTICAL AND METHOD FOR TREATMENT OF CHRONIC RHINOSINUSITIS

(76) Inventor: Michael R. Abidin, Alexandria, VA (US)

( * ) Notice: Subject to any disclaimer, the term of this patent is extended or adjusted under 35 U.S.C. 154(b) by 0 days.

(21) Appl. No.: 12/499,430

(22) Filed: Jul. 8, 2009

(51) Int. Cl.
*A01N 59/08* (2006.01)
(52) U.S. Cl. ............................................. 424/661
(58) Field of Classification Search ............... 424/661
See application file for complete search history.

(56) References Cited

U.S. PATENT DOCUMENTS

| | | | | |
|---|---|---|---|---|
| 4,990,334 | A | 2/1991 | Longino et al. | 424/401 |
| 6,664,289 | B2 * | 12/2003 | Hansen | 514/494 |
| 6,696,041 | B2 | 2/2004 | Hansen | 424/45 |

OTHER PUBLICATIONS

Stopforth, et al., Effect of Acidified Sodium Chlorite, Chlorine, and Acidic Electrolyzed Water on *Escherichia coli* O157:H7, *Salmonella*, and *Listeria monocytogenes* inoculated onto Leafy Greens, J. Food Protection 7: 625-628, 2008.*

Kim et al., Effects of a Low Concentration Hypochlorous Acid Nasal Irrigation Solution on Bacteria, Fungi, and Virus, The Laryngoscope 118: 1862-1867, 2008.*
Ritenour et al., Chlorine Use in Produce Packing Lines, University of Florida IFAS Extension, HS-761, Nov. 2002.*
Rushing et al. Post Harvest Management: Peach Skin Discoloration and Water Quality Management, http://www.ent.uga.edu/peach/peachhbk/harvest/postharvest.pdf.*
Effects Of Sodium Hypochlorite (Dakin's Solution) On Cells Of The Wound Module, Kozel et al., *Archives Of Surgery*, vol. 123, No. 4, Apr. 1988.
Diluted Dakin's Solution Support For Antisepsis Of Chronic Woounds, Century Pharmaceuticals, Inc., Fall 1999.
Material Safety Data Sheet Chlorine, Westlake CA&O, Nov. 1, 1999, Calvert City, KY.

* cited by examiner

*Primary Examiner* — James H. Alstrum-Acevedo
*Assistant Examiner* — Thor Nielsen
(74) *Attorney, Agent, or Firm* — Joseph T. Guy; Nexsen Pruet, LLC

(57) ABSTRACT

A method and solution for treating nasal infections efficiently is provided. The method includes providing a first solution comprising 0.1 to 2 wt % sodium chloride and providing a second solution comprising 2 to 8 wt % NaOCl. A first aliquot of the first solution and a second aliquot of the second solution are mixed to provide a therapeutic solution comprising at least 3-600 ppm free chlorine. The therapeutic solution is introduced into a sinus cavity containing an infection.

15 Claims, 4 Drawing Sheets

PHARMACEUTICAL AND METHOD FOR TREATMENT OF CHRONIC RHINOSINUSITIS

BACKGROUND

The present invention is related to an improved pharmaceutical formulation and method of treating chronic rhinosinusitis. More specifically, the present invention is related to an improved pharmaceutical formulation utilizing sodium hypochlorite and an improved method for administering same.

Chronic rhinosinusitis, sinusitis, chrons disease and ulcerative colitis are wide spread, related, diseases which cause significant financial impact to society. Many people are inconvenienced by these diseases.

Treatment has never been satisfactory. One complication for the ineffective treatment is that there are often two components to sinus related infections. The infection may be fungal or bacterial and treatment depends on a correct diagnosis of the source of the infection.

Hansen, in U.S. Pat. No. 6,664,289, describes a microbiocide comprising hypochlorite, chloride salts, bromide salts and a host of additional ingredients as a treatment for sinus infections. These solutions have been demonstrated to be marginally effective.

Sodium hypochlorite derivatives have been known for use in treating medical conditions. For example Pinzata and Marchetti in U.S. Pat. No. 7,056,538 teach a topical antiseptic using sodium hypochlorite at 0.015 to 20.93 wt %. This is primarily used for wound care on skin and mucous membranes. The stated advantages are less irritation and better stability at high pH with buffers. Logino et al. in U.S. Pat. No. 4,990,334 describes a topical germicidal solution for sanitizing human epidermis comprising in excess of 2 wt % sodium hypochlorite.

Though the problems associated with sinus infections has been a long standing issue there still remains a desire for a pharmaceutical for effective treatment and a method for treatment. Both an improved pharmaceutical and method for administration is provided herein.

SUMMARY OF THE INVENTION

It is an object of the present invention to provide an improved pharmaceutical formulation for treatment of sinus infections.

It is another object of the present invention to provide an improved method for administration of a pharmaceutical formulation.

A particular feature of the present invention is reliance on readily available components thereby insuring economic availability to the consumer.

Yet another feature of the present invention is that the pharmaceuticals utilized are commonly available and could be provided without a medical prescription.

These and other advantages, as will be realized, are provided in a pharmaceutical formulation for nasal administration comprising at least about 3 to about 600 ppm free chlorine.

Yet another embodiment is provided in a method for treating nasal infections. The method includes providing a first solution comprising 0.01 to 2 wt % sodium chloride and a second solution comprising 2 to 8 wt % NaOCl. A first aliquot of the first solution and a second aliquot of the second solution are mixed to provide a therapeutic solution comprising at least 3-600 ppm free chlorine. The therapeutic solution is introduced into a sinus cavity containing an infection.

Yet another embodiment is provided in a method for treating nasal infections. The method includes mixing a first solution and a second solution to form a therapeutic solution. The therapeutic solution has 3-600 ppm free chlorine. The therapeutic solution is administered to a nasal cavity of a patient.

DETAILED DESCRIPTION

Figure 1:
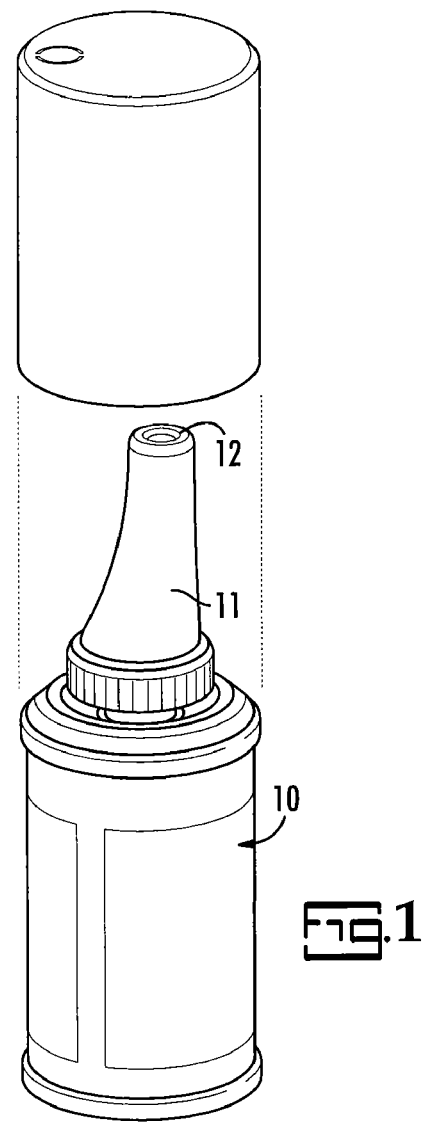
FIG. 1 schematically illustrates an aerosol can for administering a pharmaceutical formulation.

The present invention provides an improved pharmaceutical formulation for treatment of sinus infections. In particular, the present invention provides a therapeutic solution comprising free chlorine.

Sodium hypochlorite has been known for treatment of sinus infections. While not limited to any theory, the teachings in the prior art have had limited effectiveness due to inclusion of perceived necessary components which have now been demonstrated to virtually eliminate a reactive component which is effective against both bacterial and fungal infections without tissue irritation.

In particular, sodium hypochlorite provides a source of free chlorine. Free chlorine levels are diminished almost immediately by the presence of iodine, amines or metals and particularly zinc. Unfortunately, prior art formulations recite components which function to decrease free chlorine in the solution. As set forth in the Examples below the formulation recited in U.S. Pat. No. 6,696,041 to Hansen does not provide measurable amounts of free chlorine even when freshly prepared.

The present invention provides a therapeutic dose and a method of administering the therapeutic dose. Due to the inherent instability a therapeutic dose is provided in a mix-at-use arrangement comprising two solutions. More preferably, the mix-at-use arrangement consists of two solutions. The two solutions are mixed in a ratio suitable to provide 0.0000525 to 0.000525 wt % sodium hypochlorite. More preferably the two solutions are mixed in a ratio suitable to provide 0.00005 to 0.0002 wt % sodium hypochlorite. It is preferable that the sodium hypochlorite by provided in an amount suitable to provide about 3 to about 600 PPM free chlorine. More preferably, the sodium hypochlorite is provided in an amount suitable to provide about 6 to about 100 PPM free chlorine and most preferably 30 to 60 ppm free chlorine. Above about 600 ppm free chlorine there are no additional benefits realized. Below about 3 ppm free chlorine the activity diminishes toward inoperability.

The first solution, of the two solutions, comprises an aqueous solution of about 2 to about 8 wt % sodium hypochlorite. In a preferred embodiment the first solution comprises an aqueous solution of about 5 to about 5.5 wt % sodium hypochlorite. An aqueous solution with about 5.25 wt % hypochlorite is most preferred due to existing commercial availability. Below about 2 wt % sodium hypochlorite or above about 8 wt % sodium hypochlorite the mixing conditions for a suitable dose are less efficient.

The second solution is an aqueous saline solution preferably comprising about 0.01 to 2 wt % sodium chloride and more preferably 0.7 to 1.1 wt % sodium chloride.

Just prior to use an aliquot of the first solution is mixed with an aliquot of the second solution to achieve the desired concentration of sodium hypochlorite. An aliquot can be any portion up to the full amount of either or both solutions.

The therapeutic dose can be provided in a single use sample wherein a full volume of a first solution is mixed with a full volume of the second solution thereby providing a sample for a single application. The first and second solutions can be provided in separate containers or in integral containers wherein a barrier is breeched to mix the two solutions. It would be preferable to package multiple single use samples for distribution.

In an alternative embodiment the therapeutic dose can be provided in multi-use samples wherein an aliquot representing a portion of the first solution and an aliquot representing a portion of the second solution are mixed to form the therapeutic dose. The solutions can each be provided in containers comprising volumetric indicators thereby allowing the user to mix the solutions in the correct proportion by difference. For example, at least one container may contain visual marks indicating either the remaining volume or dispensed volume. In another embodiment the solutions can be provided in a metered container wherein a fixed amount of solution is dispensed sequentially. For example, at least one solution can be provided in a metered dose container wherein a fixed volume is dispensed from a larger volume.

Administration can be by any method commonly employed for introducing pharmaceuticals to the nasal cavity. Particularly mentioned methods include inhalation, spray, nebulizing, squeeze bottles, high pressure nasal irrigation from pressurized containers and the like. Administration by nebulizing, preferably a high frequency nebulizer, is most preferred.

Neither the first solution nor the second solution comprises iodide, amine or a metal and particularly zinc. In particular, the therapeutic solution does not have a detectable amount of iodide, amine or a metal. Even more preferably, neither the first solution nor the second solution comprises a detectable amount of iodide, amine or a metal. A detectable amount is intended to be below that which would significantly hinder the formation of free chloride. With regards to the present invention a detectable amount of iodide is considered to be less than 0.001 ppm iodide and more preferably less than 0.0001 ppm iodide. With regards to the present invention a detectable amount of amine is considered to be less than 0.001 ppm amine and more preferably less than 0.0001 ppm amine. With regards to the present invention a detectable amount of metal is considered to be less than 0.001 ppm metal and more preferably less than 0.0001 ppm metal. With regards to the present invention a detectable amount of zinc is considered to be less than 0.001 ppm zinc and more preferably less than 0.0001 ppm zinc. With regards to the present invention a detectable amount of chloramine is considered to be less than 0.001 ppm chloramine and more preferably less than 0.0001 ppm chloramine.

Free chlorine formation occurs almost immediately after mixing the first solution and second solution as described herein. As would be realized, the free chlorine concentration dissipates with time. It is preferable that an administrative dose be applied prior to the free chlorine concentration decreasing to below 3 ppm. Depending on initial concentration, the time for concentration dissipation is typically on the order of days. It is therefore preferably that administrative dose by given within 3 days of mixing. If a pressurized metal container is used the solution can last for many days and can last for a couple of weeks.

An administrative dose can be given when symptoms initially occur or upon exposure, or potential exposure, to infection. Administration can be a prophylactic dose or administered for treatment of symptomatic or asymptomatic patients.

The therapeutic solution may contain adjuvants such as pH buffers, additional treatment materials such as glycerin and the like. It would be apparent that additives which decrease the free chlorine level are undesirable and, if present, the time for administration after mixing needs to be adjusted accordingly. Calcium chloride is a particularly favorable pH buffer.

The therapeutic solution is preferably at a pH of 5.5 to 8.5. Within this range the sinus mucosa are not appreciably irritated. More preferably, the pH is within a range of 6-8 with a pH of about 6.5 to 7.5 being most preferred.

The therapeutic solution can be administered by a variety of techniques using a variety of delivery devices.

FIG. 1 illustrates an aerosol can for administering the therapeutic solution. The therapeutic solution is contained in a pressurized can, 10. The nozzle, 11, is manipulated thereby allowing therapeutic solution to be sprayed into the nasal cavity through an orifice, 12, preferably as a mist.

Figure 2:
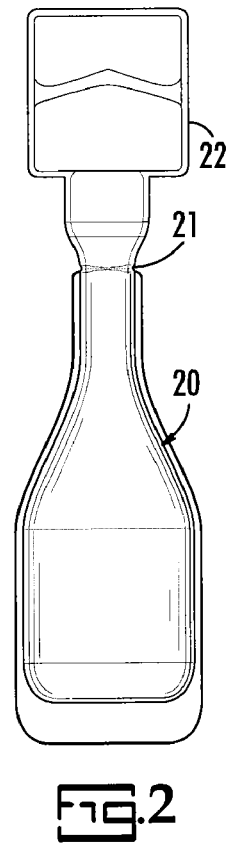
FIG. 2 schematically illustrates a single use vial for administering a pharmaceutical formulation.

FIG. 2 illustrates a single dose, single use vial, 20. The vial preferably comprises either a prepared dose or a component of the prepared dose. The vial preferable has a failure joint, 21, which breaks upon applying torque to the top portion, 22, thereby providing an orifice through which the solution is poured. In a preferred embodiment separate vials are provided wherein one vial has sodium chloride and the other vial has NaOCl. The two vials are opened and the contents mixed in the appropriate delivery device. In a particularly preferred embodiment a 240 ml solution can be prepared from single dose, single use vials and aliquots dispensed therefrom.

Figure 3:
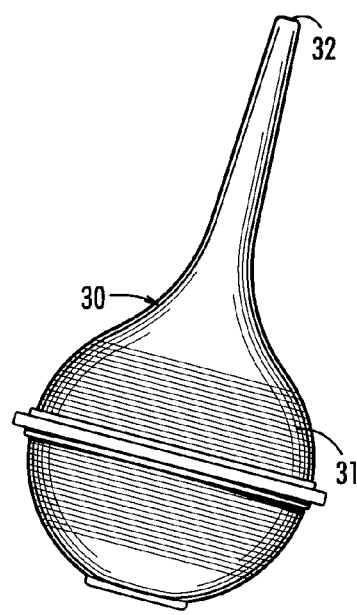
FIG. 3 schematically illustrates a bulb syringe for administering a pharmaceutical formulation.

FIG. 3 illustrates a bulb syringe, 30. Therapeutic solution is entered into the bulb, 31, and expressed into the sinus cavity by compressing the bulb and squirting material through the orifice, 32. While not limited thereto, a bulb syringe is particularly well suited for dispensing about 30 ml of solution.

Figure 4:
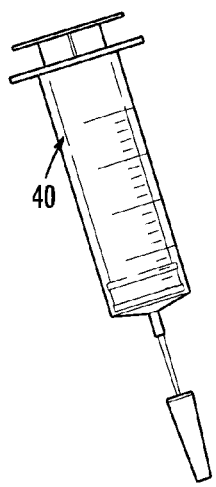
FIG. 4 schematically illustrates a syringe for administering a pharmaceutical formulation.

FIG. 4 illustrates a syringe, 40. Therapeutic solution is drawn into the syringe and the plunger is depressed to squirt solution into the nasal cavity. While not limited thereto, a bulb syringe is particularly well suited for dispensing about 20 ml of solution.

Figure 5:
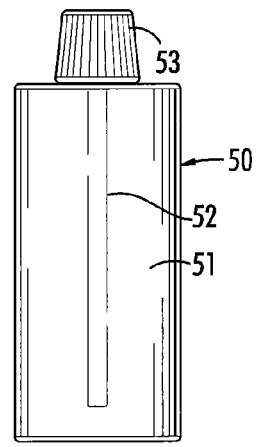
FIG. 5 schematically illustrates a squeeze bottle for administering a pharmaceutical formulation.

FIG. 5 illustrates a squeeze bottle, 50. Therapeutic solution is placed in the container, 51. As the container is squeezed the solution enters a tube, 52, wherein the solution exits through a nozzle which is not visible due to an optional protective cap, 53. A squeeze bottle is particularly well suited for containing about 240 ml and dispensing 20-30 ml at a time.

Figure 6:
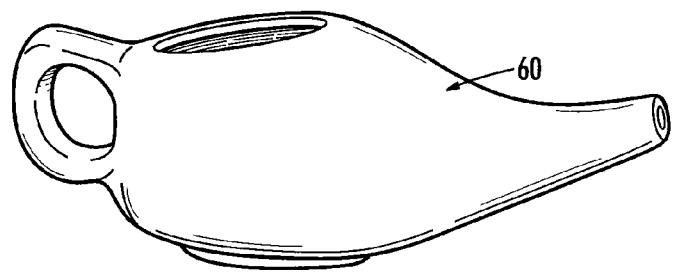
FIG. 6 schematically illustrates a neti pot for administering a pharmaceutical formulation.

FIG. 6 illustrates a neti pot, 60. Therapeutic solution is poured into the neti pot and then poured into the nasal cavity.

Figure 7:
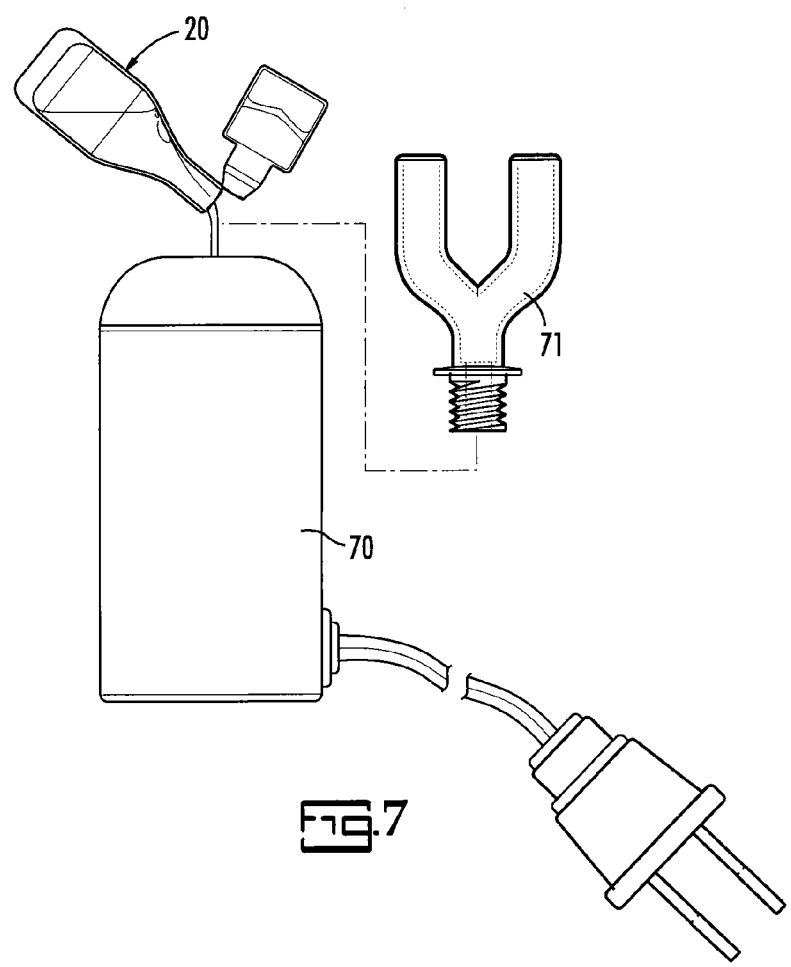
FIG. 7 schematically illustrates a method for preparing a nebulizer for administering a pharmaceutical formulation.
Figure 8:
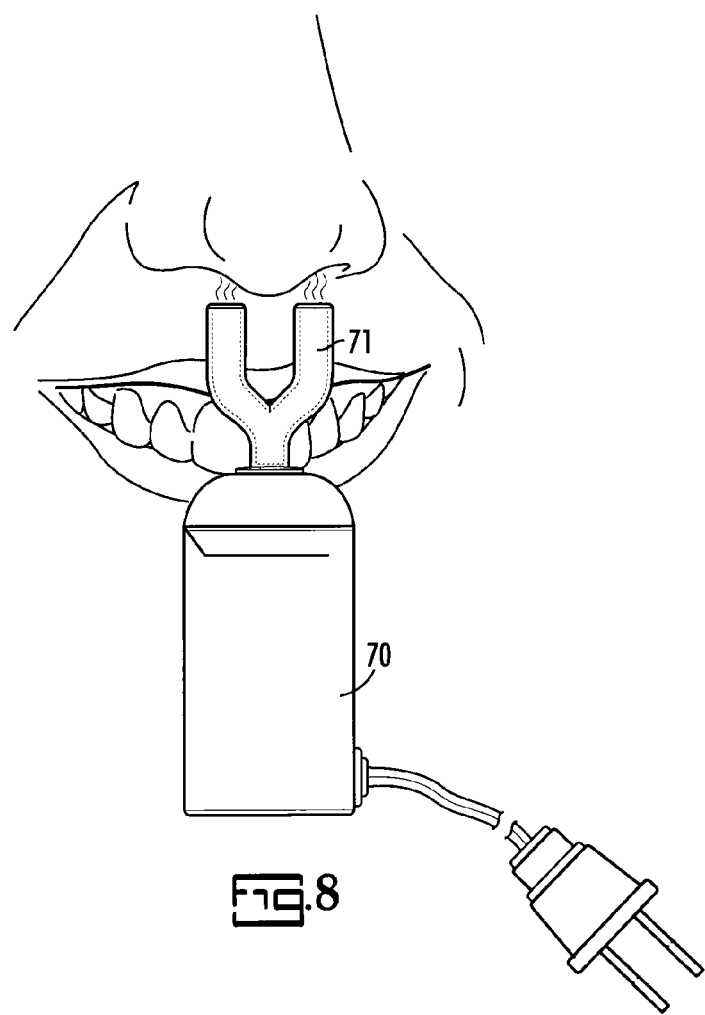
FIG. 8 schematically illustrates a method for administering a pharmaceutical formulation.

FIG. 7 illustrates a nebulizer, 70, being filled by a single dose, single use vial, 20. The nebulizer has a vapor guide, 71, wherein vapor is directed towards the sinus cavities as illustrated in FIG. 8. A liquid is vaporized in a high frequency electrical or pneumatic nebulizer to achieve a small particle size.

Examples

Representative comparative examples were prepared as described in U.S. Pat. No. 6,664,289. The sample was tested for free chlorine 10 minutes after mixing. No free chlorine was detected. An inventive sample was prepared by diluting 6% NaOCl with pharmaceutical grade saline solution 0.09 wt % sodium chloride wherein each solution lacked amines, iodide and metals. The free chlorine was measured as a function of time. The initial level was 63 ppm. At four days the free chlorine level was 56 ppm and at 10 days the free chlorine level was 48 ppm. The solutions were stored in a glass stoppered bottle in the dark. PH of the inventive sample was measured at 7.86 which was stable. Calcium chloride has been demonstrated as suitable for decreasing pH if desired.

Free chlorine was measured using a Wallace and Tiernan Series A-790 Amperometric Titrator available from Siemans Water Technologies. PH was measured using a Hanna HI 220 available from Hanna Instruments, Woodsocket, R.I.

Clinical Evaluation

A comparative sample and inventive samples were prepared for comparative testing. Inventive samples were prepared with 0.0000525 wt % sodium hypochlorite and comparative samples were prepared with 0.09 wt % sodium chloride. Samples were used with 20 patients each with similar clinical show of sinus infection. Each patient was administered 20 ml of a sample by irrigation twice a day. Patients were reevaluated at 30 days using the standard SNOT-20 procedure. Those patients receiving the inventive solution showed a 30 percent reduction in symptoms relative to those receiving the comparative sample.

The invention has been described with reference to the preferred embodiments without limit thereto. One of skill in the art would realize additional embodiment, alterations and improvements which are not specifically stated but which are within the scope of the invention as more specifically set forth in the claims appended hereto.

The invention claimed is:

1. A pharmaceutical formulation for nasal administration comprising:
   at least about 3 to about 600 ppm free chlorine and at least 0.0000525 to 0.001 wt % NaOCl.

2. The pharmaceutical formulation for nasal administration of claim 1 comprising at least 6 to no more than about 100 ppm free chlorine.

3. The pharmaceutical formulation for nasal administration of claim 2 comprising at least 30 to no more than about 60 ppm free chlorine.

4. The pharmaceutical formulation for nasal administration of claim 1 comprising at least 0.0002 to 0.0005 wt % NaOCl.

5. The pharmaceutical formulation for nasal administration of claim 1 comprising less than 0.01 wt % iodide.

6. The pharmaceutical formulation for nasal administration of claim 5 comprising less than 0.001 wt % iodide.

7. The pharmaceutical formulation for nasal administration of claim 1 comprising less than 0.01 wt % chloramine.

8. The pharmaceutical formulation for nasal administration of claim 7 comprising less than 0.001 wt % chloramine.

9. The pharmaceutical formulation for nasal administration of claim 1 comprising less than 0.01 wt % amine.

10. The pharmaceutical formulation for nasal administration of claim 9 comprising less than 0.001 wt % amine.

11. The pharmaceutical formulation for nasal administration of claim 1 comprising a first solution and a second solution.

12. The pharmaceutical formulation for nasal administration of claim 11 wherein said first solution comprises 0.1 to 2 wt % sodium chloride mixed with said second solution.

13. The pharmaceutical formulation for nasal administration of claim 12 wherein said second solution comprises 2 to 8 wt % NaOCl.

14. The pharmaceutical formulation for nasal administration of claim 11 wherein said second solution comprises 2 to 8 wt % NaOCl mixed with a first solution.

15. A pharmaceutical formulation for nasal administration comprising:
   at least about 30 to about 600 ppm free chlorine;
   at least 0.0000525 to 0.001 wt % NaOCl; and
   less than 0.01 wt % iodide.

* * * * *